(12) United States Patent
Mayer

(10) Patent No.: US 8,757,875 B2
(45) Date of Patent: Jun. 24, 2014

(54) SENSOR POSITIONING AND STABILIZING DEVICE

(76) Inventor: Peter Mayer, Duluth, MN (US)

( * ) Notice: Subject to any disclaimer, the term of this patent is extended or adjusted under 35 U.S.C. 154(b) by 117 days.

(21) Appl. No.: 13/536,055

(22) Filed: Jun. 28, 2012

(65) Prior Publication Data
US 2012/0300908 A1 Nov. 29, 2012

Related U.S. Application Data

(63) Continuation-in-part of application No. 13/359,152, filed on Jan. 26, 2012.

(60) Provisional application No. 61/436,463, filed on Jan. 26, 2011.

(51) Int. Cl.
*A61B 6/14* (2006.01)
*G03B 42/04* (2006.01)

(52) U.S. Cl.
USPC ............... 378/170; 378/38; 378/39; 378/168

(58) Field of Classification Search
CPC ......... G03B 42/02; A61C 19/04; A61B 6/145
USPC .................... 378/38, 39, 167, 168, 170, 177, 378/189–191, 204, 205, 208, 210
See application file for complete search history.

(56) References Cited

U.S. PATENT DOCUMENTS

| 4,306,866 | A | 12/1981 | Weissman |
| 5,119,410 | A * | 6/1992 | Donato ........................ 378/170 |
| 6,235,001 | B1 | 5/2001 | O'Holloran et al. |
| 6,905,244 | B2 | 6/2005 | Kilcher et al. |
| 7,070,326 | B2 | 7/2006 | Manley |
| 7,290,928 | B2 | 11/2007 | Calderwood et al. |
| 7,517,148 | B2 | 4/2009 | Ceisel et al. |

OTHER PUBLICATIONS

International Search Report and Written Opinion, issued by the International Search Authority, U.S. Receiving Office, corresponding patent application PCT/US2012/045938; mailed Oct. 1, 2012, 10 pages.

* cited by examiner

*Primary Examiner* — Anastasia Midkiff
(74) *Attorney, Agent, or Firm* — Barbara A. Wrigley; Oppenheimer Wolff & Donnelly LLP

(57) ABSTRACT

A sensor positioning and stabilizing device is provided. The sensor positioning and stabilizing device holds and stabilizes dental x-ray film or digital sensors during implant surgery with requiring a patient to bite down or manually hold it in position in order to take an x-ray.

34 Claims, 11 Drawing Sheets

SENSOR POSITIONING AND STABILIZING DEVICE

RELATED APPLICATION DATA

This application is a continuation in part of U.S. application Ser. No. 13/359,152 filed Jan. 26, 2012, which claims the benefit of U.S. Provisional Patent Application Ser. No. 61/436,463, filed Jan. 26, 2011, the entireties of which are hereby incorporated by reference.

FIELD OF THE INVENTION

This invention relates generally to positioning devices for positioning, holding and stabilizing dental x-ray film or digital sensors during implant surgery. More particularly the invention relates to an improved dental positioning and stabilizing device that does not require a patient to bite down or manually hold it in position in order to take an x-ray.

BACKGROUND OF THE INVENTION

Dentists typically use intra-oral radiographs ("x-rays") to obtain images of their patients' teeth to aid in diagnosis and treatment. In traditional oral and dental radiography, an electronic sensor is placed in the patient's mouth behind the tooth to be examined. The electronic sensor or film is secured to a positioning device or is contained within a cartridge, typically cardboard or plastic. The sensor is placed behind the tooth while the holder extends through the bite area and the patient bites down on the holder to hold the sensor in place. The x-rays pass through the tooth and imprint on the sensor, which converts the x-rays into an electrical signal. The electrical signal is transmitted over a wire connected to a computer, either directly or though a module containing intermediate processing circuitry. The computer then processes the signal to produce an image on an associated output device, such as a monitor or a printer. Similarly, x-ray film can be exposed and developed to offer the same or similar view of the desired area Numerous sensor holders have been marketed but in most conventional cases the patient must either bite down or use a finger to hold the sensor in place while the dentist or staff takes the x-ray.

Intra-oral x-rays are also required in dental implant surgery. Dental implant surgery is a procedure that replaces damaged or missing teeth with artificial teeth that look and function like real teeth. Dental implants are surgically placed in the jawbone, where they serve as the roots of missing teeth. To place the implant, the surgeon uses a dental drill including a driver and bit to drill through the patients' tissue and bone. The titanium implant includes a threaded outer portion that is screwed into the bone by the driver. An abutment portion is coupled to the titanium implant and extends out of the patient's gum and into the oral cavity. A cosmetic tooth is then attached to the abutment portion. Dental implants are often placed close to adjacent teeth and drilling into the roots of adjacent teeth while placing implants can cause irreparable harm. Consequently, it is critical for the implant to be placed as substantially parallel as possible to the roots of the adjacent teeth. It would be ideal for the dentist to take an x-ray prior to removing the drill and drill bit from the patient's jaw/bone so that she could ascertain correct and substantially parallel placement of the drilled hole. However, this task is complicated by several factors. First, the drill bit being x-rayed is high above the occlusal plane. Therefore, if a bite block sensor holder were used and a patient had to bite down in an attempt to stabilize the sensor/film holder, the drill bit would interfere with the biting action thus preventing stabilization. Second, if the patient is sedated, they are unable to follow commands to bite down or hold the sensor with their finger. Finally, asking the patient to hold the sensor/film holder may introduce bacteria into the surgical field, resulting in possible contamination of the implant and associated bone graft products.

Thus, there is a need for an x-ray positioning device that departs from the conventional methodology of having a patient bite down on or hold the sensor/film cartridge or holder in place (referred to herein as "patient interference"). There is also a need for an x-ray positioning device that improves patient comfort.

BRIEF SUMMARY OF THE INVENTION

Accordingly, this invention provides a sensor positioning and stabilizing device which overcomes the above-mentioned problems. More specifically, the invention provides a sensor/film positioning and stabilizing device wherein the device is operably coupled to the drill bit or implant driver shank after the dentist drills through the patient's jaw bone.

The invention also provides a sensor positioning and stabilizing device which does not require a patient to exert any force on the device to hold it in place.

The invention also provides a sensor positioning and stabilizing device that eliminates the need for a bite holder.

The invention also provides a sensor positioning and stabilizing device that allows for easy removal of the sensor.

The invention also provides a sensor positioning and stabilizing device that may be used with sensors of any width, length or size.

The invention includes a finger positioning tab that provides the surgeon with greater freedom in orienting the sensor.

Still further, the invention is relatively thin, which also contributes to the improved ergonomics of the sensor positioning and stabilizing device, and enables the sensor to get closer to the target area, thereby improving the image data transmitted by the sensor to the computer.

Still further, the positioning and stabilizing system includes an elongate receiving channel having a longitudinal axis, said elongate receiving channel configured to slidably receive a drill bit or a shank of an implant driver; and a dental sensor operably coupled to said elongate receiving channel such that said dental sensor is substantially parallel to the longitudinal axis of said elongate receiving channel.

Moreover, the invention includes a dental sensor operably coupled to a positioning and stabilizing system comprising an elongate receiving channel for receiving an implant drill bit or shank of an implant driver wherein the dental sensor is substantially parallel to said elongate receiving channel.

Further features of the present invention will become apparent from the following detailed description taken with reference to the accompanying drawings.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

As described above, the invention comprises a dental sensor positioning and stabilizing device for positioning, stabilizing and aligning dental x-ray sensors. The positioning device does not require a bite holder, block or other mechanism or any patient interference such as the patient biting down on the device or holding the device in place. As used herein, we refer to a "sensor" as encompassing both sensors and film.

Figure 1A:
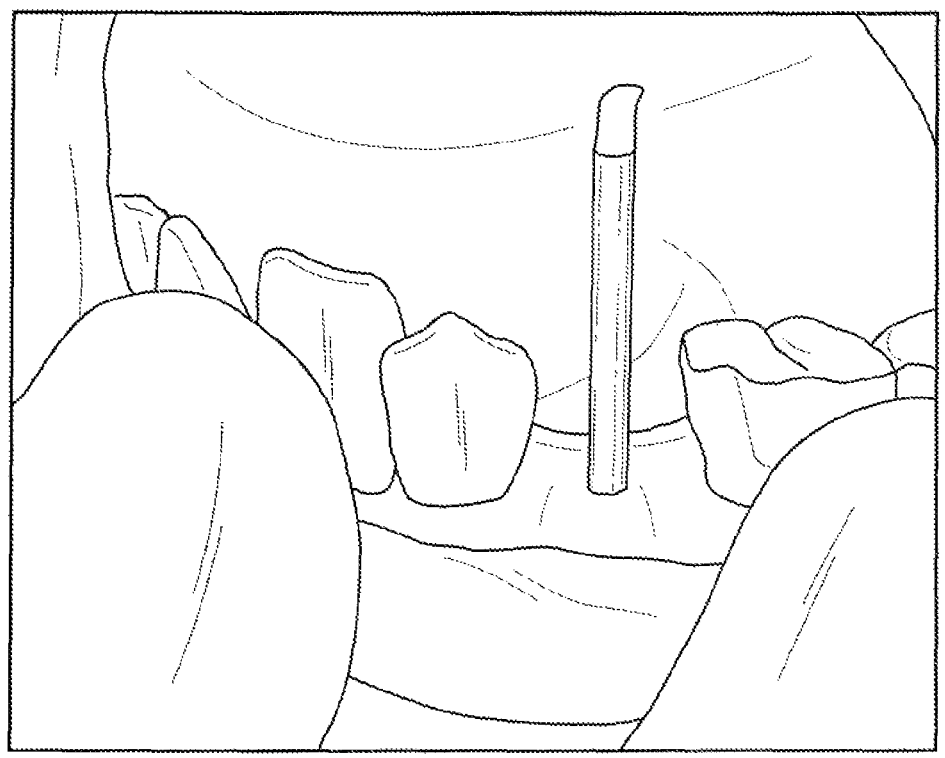
FIG. 1A shows a drill bit extending from the gums of a patient into the oral cavity.
Figure 1B:
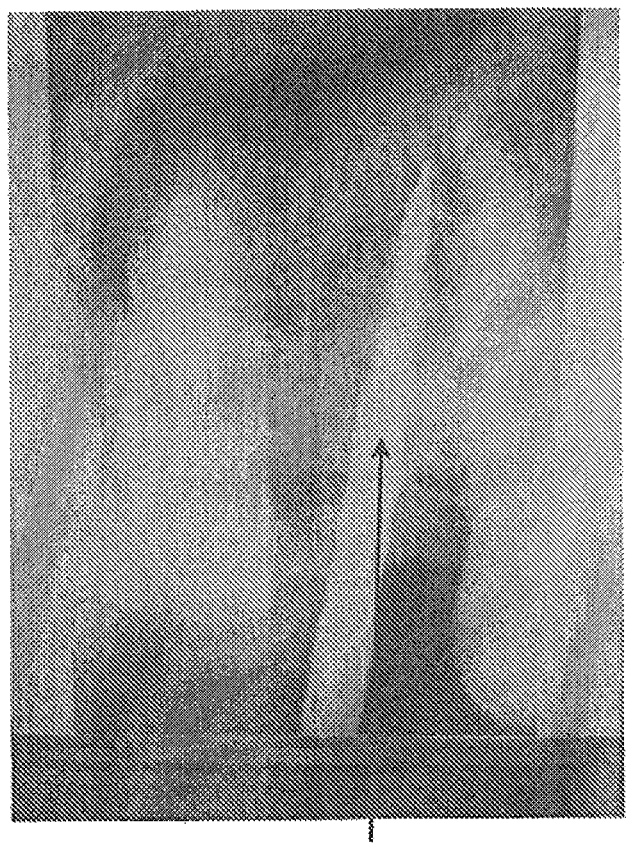
FIG. 1B is an x-ray of the misaligned drill bit of FIG. 1A.

FIG. 1A shows the oral cavity of a sedated patient after the hole for the implant has been drilled. The shank portion of the drill bit can be seen extending into the oral cavity out from the gums by 1 to 2 centimeters and ostensibly appears parallel with adjacent teeth. As can be seen in FIG. 1B, however, the drill bit is not parallel with the roots of adjacent teeth. FIG. 1B is an x-ray of a misaligned drill bit during implant surgery and highlights the problem that the present invention is designed to solve. In this case, if the drill bit was removed and an implant permanently placed the adjacent tooth root would be damaged irreparably resulting in possible tooth loss. In addition, if the implant is placed to close to an adjacent tooth at the most coronal aspect (near the crown) excessive bone loss can occur resulting in a poor aesthetic outcome.

Referring now to FIGS. 2 through 5 an exemplary dental positioning and stabilizing device in accordance with an embodiment of the present invention is shown. Positioning and stabilizing device 10 includes integrally formed elongate arms 14, 16, body 18 having first 30 and second 32 sides thereof and finger tab portion 20. Body 18 comprises an elongate receiving channel 19 having a longitudinal axis and includes aperture 21. Aperture 21 is sized to receive the shank portion of the drill bit (as best seen in FIG. 1A) that extends from the patient's gums and into the oral cavity after the implant hole has been drilled. Aperture 21 forms elongate receiving channel 19. In an embodiment of the invention aperture 21 is sized such that the inner diameter is from approximately 2.45 mm to about 2.25 mm. Elongate receiving channel 19 is designed to slidably accommodate the shank portion of a dental drill bit or implant driver shank; however, elongate receiving channel is also designed to frictionally engage the shank portion of a dental drill bit or implant driver such that after the dental positioning and stabilizing device is in position on the drill bit, the device is securely fixed on the drill bit.

Arms 14, 16 each include resilient flanges 22, 24, respectively. Flanges 22, 24 act to operably and resiliently connect elongate arms to cylindrical-shaped body 18. Those of skill in the art will appreciate that while body 18 is depicted as being circular or cylindrical-shaped many other shapes are contemplated and fall within the scope of the invention. Elongate arms 14, 16 are C-shaped in cross section and include sensor channels 26 which form clamps that are designed to grip the sensor and stabilize it in position. When stabilized in position, the sensor is substantially parallel to the longitudinal axis of elongate receiving channel 19. By substantially parallel we mean that the sensor can be moved from being precisely parallel to the longitudinal axis of the elongate receiving channel to an acute angle off from the longitudinal axis of the elongate receiving channel 19. In other words, the sensor can be positioned at an acute angle from the longitudinal axis of the elongate receiving channel, the acute angle being from 0.1 degrees to about 45 degrees.

Positioning device is formed from a resilient or flexible material such as polypropylene or the like such that flanges 22, 24 resiliently and easily pivot elongate arms 14, 16 from an initial position (shown) to a second open position. While in the second position, sensor channels 26 accommodate the dental sensor and then resiliently return to the initial position in which channels 26 snuggly surround the sensor so that it is stabilized within channels 26. Arms 14, 16 are integrally formed with flanges 22, 24. Flanges 22, 24 are integrally formed with and extend laterally from first side 30 of elongate channel 18. Resilient flanges 22, 24 accommodate the resilient and flexible movement of arms 14, 16 from the initial position to a second position, as noted above. Those of skill in the art will appreciate that numerous embodiments that are within the scope of the invention are possible. For example, flanges 22 and 24 need not be integrally formed with body 18 but rather may be operably connected by adhesive, connecting tabs and other such means without departing from the scope of the invention. Similarly, one flange may extend laterally from a central body. Such one flange may include two resilient arms having channels which receive the sensor or film. Further, those of skill in the art will appreciate that any system designed to hold a dental sensor substantially parallel to the longitudinal axis of the elongate receiving channel and which does not require patient interference is within the scope of the invention.

Finger tab portion 20 is operably connected to and integrally formed with the second side 32 of body 18. Those of skill in the art will appreciate that finger tab portion need not be integrally formed with circumferential body 18 but rather may be operably connected by adhesive, connecting tabs and other such means without departing from the scope of the invention. Finger tab portion 20 extends generally radially outward and slightly downward from said circumferential body 19. Finger tab portion and includes upper 36 and lower 38 elements and tab portion 44. Upper element 36 includes a first generally straight portion 34 that extends radially outward from second side 32 of circumferential body 18. Lower element 38 includes curvilinear portion 40 and extends radially outward and downward from second side 32 of circumferential body 18. Tab portion 44 extends laterally from upper and lower elements 36, 38. Upper and lower elements 36, 38 and tab portion 44 are ergonomically designed so that the surgeon can easily grasp and precisely position the sensor positioning and stabilizing device 10 behind the teeth and an x-ray of the drill bit in the drilled hole can be taken (as best seen in FIG. 1B).

Figure 2:
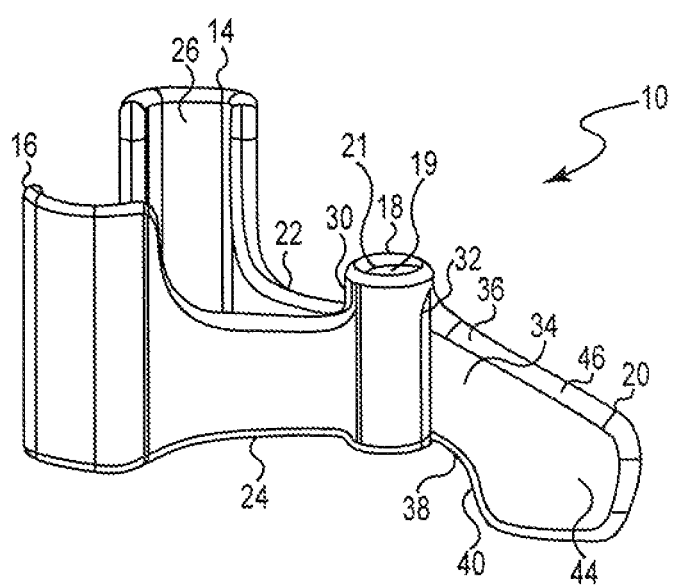
FIG. 2 is a perspective view of the dental sensor positioning and stabilizing device in accordance with the invention.
Figure 3:
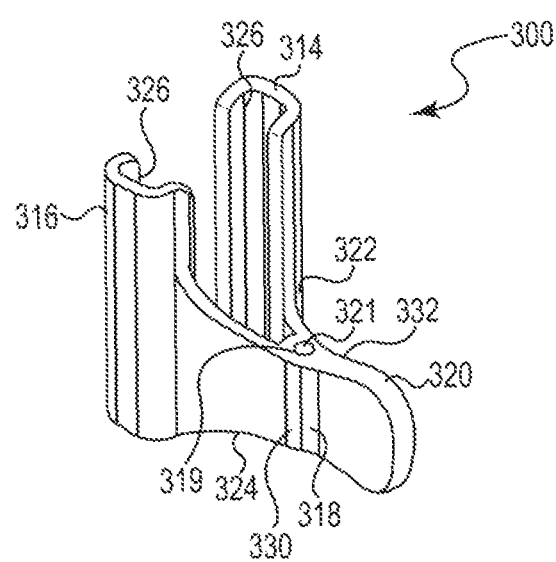
FIG. 3 is a perspective view of a first alternative embodiment of the dental sensor positioning and stabilizing device in accordance with the invention.

FIG. 3 depicts an embodiment of a sensor positioning and stabilizing device 300 in accordance with the invention in which the elongate receiving channel 319 is substantially longer in length than the embodiment depicted in FIG. 2 and finger tab portion 320 extends radially outward and is substantially perpendicular to elongate arms 314, 316. Those of skill in the art will appreciate however that elongate receiving channel 319 may be of any length to accommodate varying drill bit lengths and patient dental profiles. Positioning device 300 includes integrally formed elongate arms 314, 316, body 318 having first 330 and second 332 sides thereof and finger tab portion 320. Body 318 comprises an elongate receiving channel 319 with aperture 321. Aperture 319 is sized to receive a drill bit or shank portion of an implant driver (as best seen in FIG. 1A) that extends from the patient's gums and into the oral cavity after the implant hole has been drilled. Elongate receiving channel 319 is designed to slidably accommodate the shank portion of a dental drill bit.

Arms 314, 316 each include resilient flanges 322, 324, respectively. Flanges 322, 324 act to operably and resiliently connect elongate arms to circumferential body 318. Elongate arms 314, 316 are C-shaped in cross section and include sensor channels 326 which form clamps that are designed to grip the sensor and stabilize it in position. Positioning device is formed from a resilient or flexible material such as polypropylene or the like such that flanges 322, 324 resiliently and easily pivot elongate arms 314, 316 from an initial position (shown) to a second open position. While the arms are in the open position, sensor channels 326 accommodate the dental sensor or film and then resiliently return to the initial position in which channels 326 snuggly surround the sensor so that it is stabilized within channels 26. Arms 314, 316 may be integrally formed with flanges 322, 324. Flanges 322, 324 in turn are integrally formed with and extend laterally from first side 330 of elongate channel 318. Resilient flanges 322, 324 accommodate the resilient and flexible movement of arms 314, 316 from the initial position to a second position, as noted above. Those of skill in the art will appreciate that numerous embodiments that are within the scope of the invention are possible. For example, flanges 322 and 324 need not be integrally formed with body 318 but rather may be operably connected by adhesive, connecting tabs and other such means without departing from the scope of the invention. Similarly as described above, one flange may extend laterally from a central body. Such one flange may include two resilient arms having channels which receive the sensor or film.

As depicted in FIG. 3, finger tab portion 320 is operably connected to and integrally formed with the second side of body 318. Finger tab portion 320 extends radially outward from circumferential body 318. Finger tab portion includes tab portion 344. Tab portion 344 extends laterally from straight portion 334 and is designed so that the surgeon can easily grasp and precisely position the sensor positioning and stabilizing device 300 behind the teeth and an x-ray of the drill bit in the drilled hole can be taken (as best seen in FIG. 1B).

Figure 4:
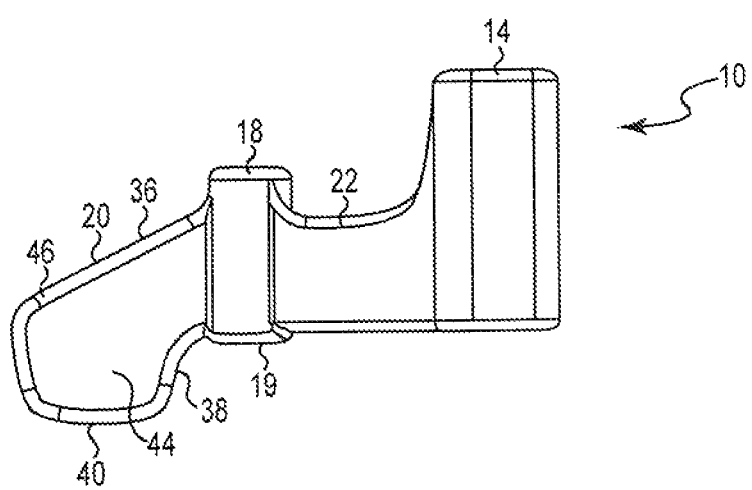
FIG. 4 is a side view of the dental sensor positioning and stabilizing device in accordance with the invention.

FIG. 4 is a side view of the dental sensor positioning and stabilizing device 10 in accordance with the invention with detail regarding finger tab portion 20. Finger tab portion 20 includes tab body 40. Finger tab portion 20 extends generally radially outward and slightly downward from said circumferential body 19. Finger tab portion and includes upper 36 and lower 38 elements and tab portion 44. Upper element 36 includes a first generally straight portion 34 that extends radially outward from second side 32 of circumferential body 18. Lower element 38 includes curvilinear portion 40 and extends radially outward and downward from second side 32 of circumferential body 18. Tab portion 44 extends laterally from upper and lower elements 36, 38. Upper and lower elements 36, 38 and tab portion 44 are ergonomically designed so that the surgeon can easily grasp and precisely position the sensor positioning and stabilizing device 10 behind the teeth and an x-ray of the drill bit in the drilled hole can be taken (as best seen in FIG. 1B). Finger tab portion 20 and thus dental sensor position and stabilizing device 10 may be oriented upwards or downwards depending on where the implant will be located, i.e. upper or lower gum line. Optional raised ridge 46 surrounds tab portion 44 and is designed to allow the surgeon to securely grip finger tab portion 20.

Figure 5:
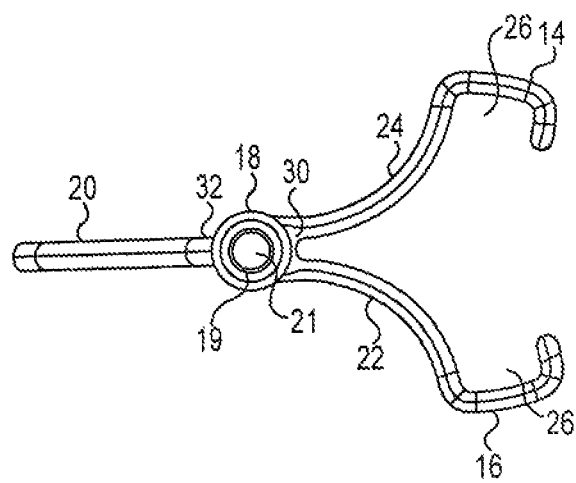
FIG. 5 is a top view of the dental sensor positioning and stabilizing device in accordance with the invention.

FIG. 5 depicts a top view of the sensor positioning and stabilizing device 10 in accordance with the invention showing detail regarding aperture flanges 22, 24 and C-shaped in cross section sensor channels 26.

Figure 6A:
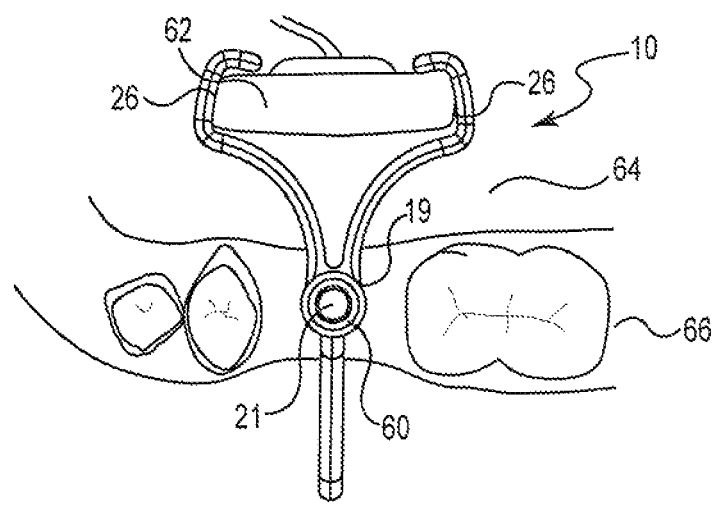
FIG. 6A is a top view of the dental sensor positioning and stabilizing device in accordance with the invention attached to an implant driver with the sensor placed behind the dental arch.

FIG. 6A is a top view of the dental sensor positioning and stabilizing device 10 in use in accordance with one aspect of the invention. As can be seen, the positioning and stabilizing device 10 has been slidably received by an implant drill bit 60 through aperture 21 and into elongate receiving channel 19. Sensor 62 is received within and held by sensor channels 26 thus allowing it to be easily positioned behind the dental arch 64 above the occlusal plane 66.

Figure 6B:
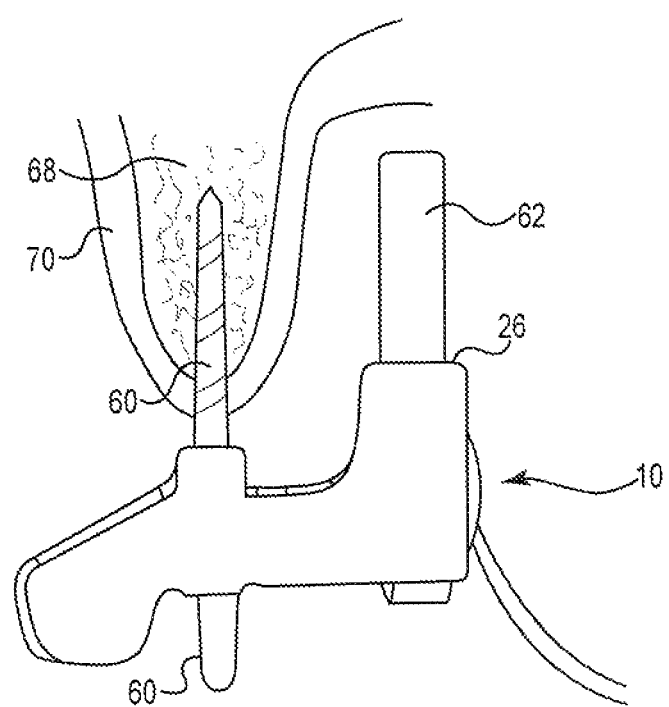
FIG. 6B is a side view of the dental sensor positioning and stabilizing device in accordance with the invention with the device attached to a drill bit with the sensor place behind the dental arch.
Figure 8:
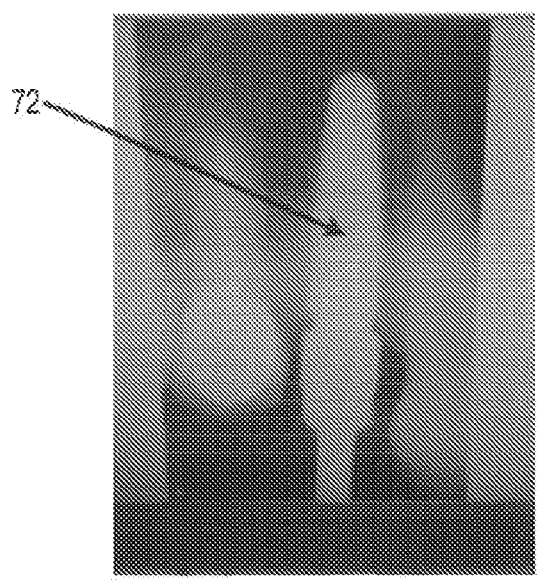
FIG. 8 is an x-ray of an implant that is correctly aligned in relation to adjacent teeth.

FIG. 6B is a side view of the dental sensor positioning and stabilizing device 10 in accordance the invention in operation. The dental surgeon first drills a hole through the patient's mucosa 70 and bone 68 as close as possible to a parallel position next to adjacent teeth. As can be seen, the positioning and stabilizing device 10 is then slidably received by the implant drill bit 60 as also seen in FIG. 6A. Sensor 62 is positioned within sensor channels 26 and is moveably positioned from left to right by the finger tab portion 20 behind the dental arch 64 above the occlusal plane 66 into the correct position for taking an x-ray of the drill bit. With the drill bit in position, the dental surgeon next takes an x-ray and views it on a computer screen. If the drill bit is positioned parallel to adjacent tooth structure, the dental sensor positioning device is removed from the drill bit 60 and a second, larger drill bit is used to enlarge the pre-existing hole. The process of taking an x-ray may be repeated as many times as the surgeon desires to ensure that the hole into which the dental implant will be secured is parallel to adjacent tooth structure. If the x-ray shows that the initial drilling of the drill bit is not parallel then the sensor positioning device is removed and a second, larger drill bit is used to drill through the pre-existing hole to correct the path of the hole. The sensor positioning device is then place on the drill bit (with the drill removed) and another x-ray is taken to verify position. The dental surgeon may repeat the process as many times as desired to verify that the drill bit is correctly positioned and substantially parallel to the adjacent teeth. The drill bit is then removed and replaced with implant 72 as best seen in FIG. 8.

Figure 7A:
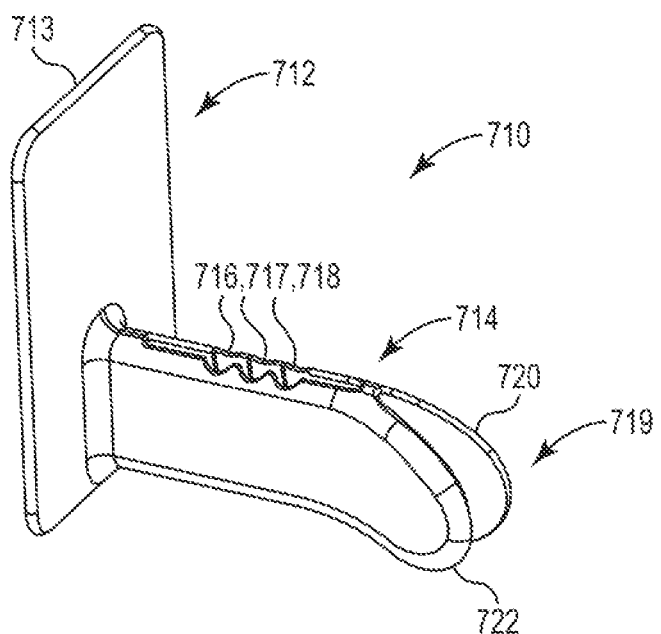
FIG. 7A is a perspective view of a second embodiment of a dental sensor positioning and stabilizing device in accordance with the invention.
Figure 7B:
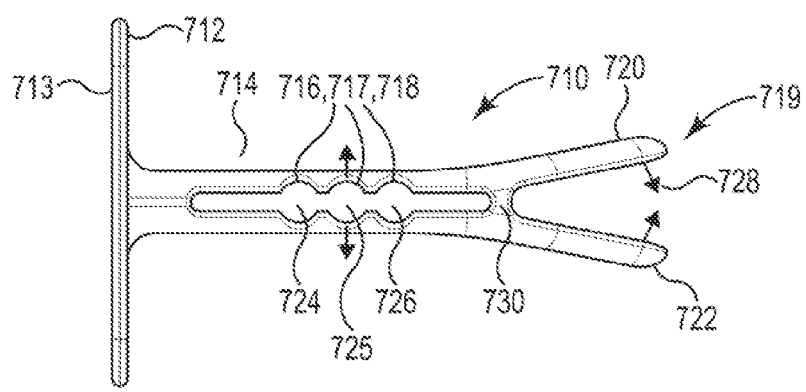
FIG. 7B is a top view of the embodiment of FIG. 7A.

Referring now to FIGS. 7A and 7B an alternative embodiment of the dental sensor positioning and stabilizing device 710 in accordance with the invention is shown. Dental sensor positioning and stabilizing device 710 broadly includes sensor holder 712 having sensor face 713; body 714 defining a plurality of elongate receiving channels positioned perpendicular to a longitudinal axis 719 thereof, and actuator portion 719 defining first and second resilient arms 720, 722. Body 714 may be integrally formed with sensor holder 712, however, those of skill in the art will appreciate that body 714 can also be adhesively joined or snap fitted with sensor holder 712.

In preferred constructions, sensor holder 712, body 714 and actuator portion 719 may be integrally-formed as a single component. For example, in one construction, sensor holder 712, body 714 and actuator portion 719 are injection molded as a single part in one manufacturing step. By integrally-molding the dental sensor positioning and stabilizing device 710, the overall cost of the device is reduced. If the dental sensor positioning and stabilizing device 710 is integrally formed, a single material may be used in a single injection molding step. Alternatively, two different materials or any number of materials could be used to form the device. For example, a co-molding or two step injection molding process may also be employed.

Sensor face 713 preferably includes a sheath (not shown) that will be adhesively and removably coupled to sensor face 713 for holding a dental sensor (not shown). A plurality of elongate receiving channels 716, 717, 718 are positioned in body 714 perpendicular to a longitudinal axis 719 thereof and are structured to accommodate a drill bit. Drill bit may be positioned in first, second or third receiving channel depending on the particular patient anatomy involved.

Apertures 724, 725 and 726 are sized to receive the shank portion of a drill bit (as best seen in FIG. 1A) that extends from the patient's gums and into the oral cavity after the implant hole has been drilled. Apertures 724, 725, 726 form elongate receiving channels 716, 717, 718. In an embodiment of the invention, apertures 724, 725, 726 are sized such that the inner diameter is from approximately 2.45 mm to about 2.25 mm. Elongate receiving channels 716, 717, 718 are structured to slidably accommodate the shank portion of a dental drill bit or implant driver shank; however, elongate receiving channels 716, 717, 718 are also designed to frictionally engage the shank portion of a dental drill bit or implant driver such that after the dental positioning and stabilizing device is in position on the drill bit, the device is securely fixed on the drill bit.

Arms 720, 722 may be integrally formed with body 714, however, those of skill in the art will appreciated that any structure that operably coupled arms 720, 722 to body 714 may be employed. Arms 720, 722 act to operably and resiliently couple with body 714. Positioning device 710 is formed from a resilient or flexible material such as polypropylene or the like such that arms 720, 722 resiliently and easily move from an initial non-actuated position (shown) to a second actuated position 728 as shown by arrows as best seen in FIG. 7B. When the surgeon pinches the arms to actuate the device to the second position, elongate receiving channels 716, 717, 718 open in response thereof allowing easy placement of the dental positioning and stabilizing device 710 over the dental drill bit or implant driver dental and then resiliently return to the initial non-actuated position in which elongate receiving channels 716, 717, 718 snuggly surround the sensor so that it is stabilized within channels 716, 717, 718. As can best be seen in FIG. 7B, coupling mechanism 730 transmits the actuation of arms 720, 722 from the initial non-actuated position to the second actuated position to elongated receiving channels 716, 717, 718.

Those of skill in the art will appreciate that numerous embodiments that are within the scope of the invention are possible. For example, arms 720, 722 and sensor holder 712 need not be integrally formed with body 714 but rather may be operably connected by adhesive, connecting tabs and other such means without departing from the scope of the invention.

In operation the dental positioning and stabilizing device of FIGS. 7A and 7B are used as follows. The dental surgeon first drills a hole through the patient's mucosa 70 and bone 68 as close as possible to a parallel position next to adjacent teeth. The surgeon grasps actuator portion 720 and pinches it inwardly to move it from the non-actuated initial position to the actuated position which causes elongate channels to open so that the positioning and stabilizing device 710 may then slidably be received by an implant drill bit received through one of elongate receiving channels 716, 717, 718 depending on the particular patient anatomy. A sensor (not shown) is positioned within a sheath (not shown) that is operably coupled to the face 713 of the sensor holder 712 and may be moveably positioned from left to right by the actuator portion 719 behind the dental arch 64 above the occlusal plane 66 into the correct position for taking an x-ray of the drill bit. With the drill bit in position, the dental surgeon next takes an x-ray and views it on a computer screen. If the drill bit is positioned parallel to adjacent tooth structure, the dental sensor positioning device is removed from the drill bit and a second, larger drill bit is used to enlarge the pre-existing hole. The process of taking an x-ray may be repeated as many times as the surgeon desires to ensure that the hole into which the dental implant will be secured is parallel to adjacent tooth structure. If the x-ray shows that the initial drilling of the drill bit is not parallel then the sensor positioning device is removed and a second, larger drill bit is used to drill through the pre-existing hole to correct the path of the hole. The sensor positioning device is then place on the drill bit (with the drill removed) and another x-ray is taken to verify position. The dental surgeon may repeat the process as many times as desired to verify that the drill bit is correctly positioned and substantially parallel to the adjacent teeth. The drill bit is then removed and replaced with implant 72 as best seen in FIG. 8.

FIG. 8 depicts an x-ray taken with the sensor positioning and stabilizing device 10, 710 in accordance with the invention. As can be seen and compared to the angled drill bit depicted in FIG. 1B the implant 72 can be seen to be correctly positioned and substantially parallel to the adjacent teeth.

Advantageously, the sensor positioning and stabilizing device in accordance with the invention is supported by a drill bit thus eliminating the need to have a patient bite down on, manually hold the sensor/film cartridge or holder in place, or otherwise stabilize the device. The sensor positioning and stabilizing device in accordance requires no patient interference.

While the invention has been particularly shown and describe with respect to exemplary embodiments thereof, those of ordinary skill in the art will appreciate and understand that changes in form and details may be made without departing from the scope and spirit of the invention.

What is claimed is:

1. A positioning and stabilizing device for positioning and stabilizing sensors for intra-oral x-rays comprising: a substantially cylindrical body defining an elongate receiving channel therewithin structured to slidably and removably accommodate a portion of an elongate dental implant implement selected from a dental drill shank, a dental drill bit or an implant driver, said body including a longitudinal axis; at least one elongate arm operably connected to a first side of said body, said elongate arm extending laterally from a first side of said cylindrical body; and a finger tab portion operably connected to a second side of said body.

2. The positioning and stabilizing device of claim 1 wherein said at least one elongate arm includes a resilient flange portion resiliently connected to said first side of said body.

3. The positioning and stabilizing device of claim 2 wherein said resilient flange portion extends substantially perpendicular to said body.

4. The positioning and stabilizing device of claim 2 wherein said at least one elongate arm includes a C-shaped in cross section channel for holding a dental sensor.

5. The positioning and stabilizing device of claim 4 wherein said C-shaped in cross section channel is parallel to the longitudinal axis of said body.

6. The positioning and stabilizing device of claim 3 wherein said at least one elongate arm comprises first and second elongate arms.

7. The positioning and stabilizing device of claim 6 wherein said flange portion allows said first and second arms to resiliently pivot from an initial position to a second position.

8. The positioning and stabilizing device of claim 1 wherein said finger tab portion is operably connected to said second side of said cylindrical body.

9. The positioning and stabilizing device of claim 1 wherein said finger tab portion extends radially outward from said second side of said cylindrical body.

10. The positioning and stabilizing device of claim 1 wherein said finger tab portion further comprises upper and lower elements.

11. The positioning and stabilizing device of claim 10 wherein said lower element has a curvilinear profile.

12. The positioning and stabilizing device of claim 10 wherein said upper element has a straight profile.

13. A positioning and stabilizing system for positioning and stabilizing sensors for intra-oral x-rays comprising: an elongate receiving channel having a longitudinal axis, said elongate receiving channel configured to slidably and removably receive a portion of an elongate dental implant implement; and a dental sensor holding device operably coupled to said elongate receiving channel such that said dental sensor holding device is structured to hold a dental sensor substantially is parallel to the longitudinal axis of said elongate receiving channel.

14. The positioning and stabilizing system of claim 13 wherein said dental sensor is stabilized without having a patient apply force to said sensor.

15. The positioning and stabilizing system of claim 13 further comprising at least one elongate arm operably connected to said elongate receiving channel.

16. The positioning and stabilizing system of claim 15 wherein said at least one elongate arm comprises a resilient material.

17. The positioning and stabilizing system of claim 15 wherein said at least one elongate arm is operably coupled to said dental sensor holding device, said dental sensor holding device comprising two substantially C-shaped in cross section channels for receiving said dental sensor.

18. The positioning and stabilizing system of claim 17 wherein said C-shaped in cross section channels are parallel to the longitudinal axis of said elongate receiving channel.

19. A positioning and stabilizing system for positioning and stabilizing sensors for intra-oral x-rays comprising: a dental sensor holding device operably coupled to a positioning and stabilizing system, said system comprising an elongate receiving channel for receiving at least a portion of an elongate dental implant implement wherein said dental sensor holding device is structured to hold a dental sensor substantially parallel to said elongate receiving channel.

20. The positioning and stabilizing system of claim 16 wherein patient interference is not required to stabilize the dental sensor.

21. A positioning and stabilizing system for positioning and stabilizing sensors for intra-oral x-rays comprising: an elongate receiving channel having a longitudinal axis, said elongate receiving channel configured to slidably and removably receive an elongate, substantially cylindrical dental implant implement; a dental sensor holding device operably coupled to said elongate receiving channel such that said dental sensor holding device is positioned from parallel to the longitudinal axis of the elongate receiving channel to about 10 degrees offset from the longitudinal axis of said elongate receiving channel.

22. A positioning and stabilizing system for positioning and stabilizing sensors for intra-oral x-rays comprising: an elongate receiving channel having a longitudinal axis, said elongate receiving channel configured to slidably and removably receive an elongate dental implant implement; a dental sensor holding member operably coupled to said elongate receiving channel such that said dental sensor holding member is positioned at an acute angle from the longitudinal axis of the elongate receiving channel.

23. The positioning and stabilizing system of claim 22 wherein said acute angle is from about 0.01 degree to about 10 degrees.

24. A positioning and stabilizing system for positioning and stabilizing sensors for intra-oral x-rays comprising: an actuator portion, said actuator portion movable between an actuated position and a non-actuated position; a body portion operably coupled to the actuator portion, said body portion defining at least one elongate receiving channel movable between closed position and an open position in response to movement of the actuator portion from the non-actuated position to the actuated position, said elongate receiving channel configured to slidably and removably receive a portion of an elongate dental implant implement when said at least one elongate channel moves from the closed position to the open position; and a sensor holder operably coupled to said body and configured to receive a sensor thereon and hold said sensor substantially parallel to a longitudinal axis of said elongate receiving channel.

25. The positioning and stabilizing system of claim 24 wherein said actuator portion includes two finger-grasping resilient arms.

26. The positioning and stabilizing system of claim 24 wherein said sensor holder, said body and said actuator portion are integrally formed.

27. The positioning and stabilizing system of claim 24 wherein at least one of said sensor holder, said body and said actuator portion are non-integrally formed.

28. The positioning and stabilizing system of claim 24 further comprising a sheath operably coupled to a face of said sensor holder.

29. The positioning and stabilizing system of claim 28 wherein said sheath is adhesively coupled to said face of said sensor holder.

30. The positioning and stabilizing system of claim 28 wherein said sheath is removably coupled to said face of said sensor holder.

31. The positioning and stabilizing system of claim 13 wherein said elongate dental implement is selected from a dental drill shank, a dental drill bit, and an implant driver.

32. The positioning and stabilizing system of claim 19 wherein said elongate dental implement is selected from a dental drill shank, a dental drill bit, and an implant driver.

33. The positioning and stabilizing system of claim 21 wherein said elongate dental implement is selected from a dental drill shank, a dental drill bit, and an implant driver.

34. The positioning and stabilizing system of claim 24 wherein said elongate dental implement is selected from a dental drill shank, a dental drill bit, and an implant driver.

* * * * *